(12) United States Patent
Kamabuchi et al.

(10) Patent No.: US 6,818,379 B2
(45) Date of Patent: Nov. 16, 2004

(54) SULFONIUM SALT AND USE THEREOF

(75) Inventors: Akira Kamabuchi, Ashiya (JP); Kaoru Araki, Kyoto (JP)

(73) Assignee: Sumitomo Chemical Company, Limited, Osaka (JP)

(*) Notice: Subject to any disclaimer, the term of this patent is extended or adjusted under 35 U.S.C. 154(b) by 0 days.

(21) Appl. No.: 10/305,151

(22) Filed: Nov. 27, 2002

(65) Prior Publication Data

US 2003/0148211 A1 Aug. 7, 2003

(30) Foreign Application Priority Data

Dec. 3, 2001 (JP) .................................... 2001-368237

(51) Int. Cl.$^7$ .............................. G03F 7/004; C08F 2/46
(52) U.S. Cl. .................... 430/270.1; 430/905; 430/921; 522/31
(58) Field of Search .............................. 430/270.1 UD, 430/905, 921, 270.1, 922; 522/31, 25; 568/25, 28, 38; 570/182

(56) References Cited

U.S. PATENT DOCUMENTS

| | | |
|---|---|---|
| 5,554,664 A | 9/1996 | Lamanna et al. |
| 6,348,297 B1 | 2/2002 | Uetani et al. |
| 6,383,713 B1 | 5/2002 | Uetani et al. |
| 2002/0006582 A1 | 1/2002 | Inoue et al. |
| 2003/0008241 A1 * | 1/2003 | Sato et al. |

OTHER PUBLICATIONS

Research Disclosure, vol. 437, pp. 1568–1569 (Sep. 2000).

* cited by examiner

*Primary Examiner*—Rosemary Ashton

(57) ABSTRACT

The present invention provides a sulfonium salt represented by the following formula (I):

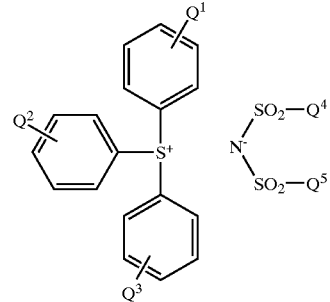

(I)

wherein $Q^1$, $Q^2$ and $Q^3$ each independently represent hydrogen, hydroxy, alkyl having 1 to 6 carbon atoms, or alkoxy having 1 to 6 carbon atoms, but all of $Q^1$, $Q^2$ and $Q^3$ are not the same; and $Q^4$ and $Q^5$ each independently represent perfluoroalkyl having 1 to 8 carbon atoms. The present invention also provides a chemical amplifying type positive resist composition having the sulfonium salt above and a resin which contains a structural unit having a group that is unstable to acid and which is insoluble or slightly soluble by itself in an aqueous alkali, but becomes soluble in the aqueous alkali by an action of acid. The present invention further provides a polymerization initiator composition having the sulfonium salt above and a sensitizer.

10 Claims, No Drawings

SULFONIUM SALT AND USE THEREOF

This nonprovisional application claims priority under 35 U.S.C. §119(a) on Patent Application No. 2001-368237 filed in JAPAN on Dec. 3, 2001, which is herein incorporated by reference.

BACKGROUND OF THE INVENTION

The present invention relates to a novel sulfonium salt, a chemical amplifying type resist composition for use in semiconductor microfabrication, and a polymerization initiator composition.

Semiconductor microfabrication employs a lithography process using a resist composition. In lithography, theoretically, the shorter the exposure wavelength becomes, the higher the resolution can be made, as expressed by Rayleigh's diffraction limit formula. The wavelength of an exposure light source for lithography used in the manufacture of semiconductor devices has been shortened year by year as g line having a wavelength of 436 nm, i line having a wavelength of 365 nm, KrF excimer laser having a wavelength of 248 nm and ArF excimer laser having a wavelength of 193 nm. $F_2$ excimer laser having a wavelength of 157 nm seems to be promising as the next-generation exposure light source. Further, as the exposure light source of the subsequent generation, extreme ultraviolet (EUV) ray having a wavelength of 13 nm has been proposed as the exposure light source following the 157 nm-wavelength $F_2$ excimer laser.

Since light sources having shorter wavelength than that of g line and i line, such as excimer laser and the like have low illumination, it is necessary to enhance the sensitivity of a resist. Consequently, there are used so-called chemical amplification type resists utilizing the catalytic action of an acid produced from a sulfonium salt by exposure and containing a resin having a group being dissociated by this acid.

However, conventionally known sulfonium salts disclosed in, for example, WO96/27584 or Research Disclosure Vol. 437 September, 1568 (2000), involve the problem that those of the type having high sensitivity provide an unsatisfactory cross-sectional view of resist particularly with a rounded head, while, conversely, those of the type capable of providing a good cross-section view of resist have low sensitivity.

The object of the present invention is to provide a novel sulfonium salt as well as to provide a chemical amplifying type positive resist composition comprising the sulfonium salt and a resin component, which resist composition is suitable for lithography employing ArF or KrF excimer laser for example and has sensitivity in good balance with a cross-sectional view of resist.

As a result of intensive study made by the inventors of the present invention, they have found that use of a specific sulfonium salt makes it possible to resolve the foregoing problem, and have completed the present invention.

SUMMARY OF THE INVENTION

That is, the present invention is directed to:

(1) A sulfonium salt represented by the following formula (I) (hereinafter referred to as "the present sulfonium salt")

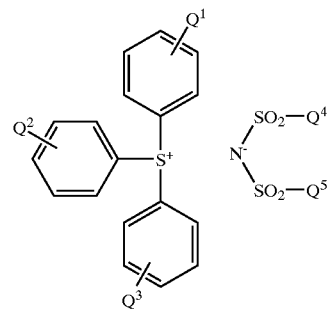

wherein $Q^1$, $Q^2$ and $Q^3$ each independently represent hydrogen, hydroxy, alkyl having 1 to 6 carbon atoms, or alkoxy having 1 to 6 carbon atoms, but all of $Q^1$, $Q^2$ and $Q^3$ are not the same; and $Q^4$ and $Q^5$ each independently represent perfluoroalkyl having 1 to 8 carbon atoms.

(2) The sulfonium salt according to (1), wherein in the formula (I), one of $Q^1$, $Q^2$ and $Q^3$ is methyl and each of the other two is hydrogen.

(3) The sulfonium salt according to (1), wherein in the formula (I), one of $Q^1$, $Q^2$ and $Q^3$ is tert-butyl and each of the other two is hydrogen.

The present invention is also directed to:

(4) A chemical amplifying type positive resist composition comprising: a resin which contains a structural unit having a group that is unstable to acid and which is insoluble or slightly soluble by itself in an aqueous alkali, but becomes soluble in the aqueous alkali by an action of acid; and the present sulfonium salt (hereinafter referred to as "the present resist composition").

(5) The chemical amplifying type positive resist composition according to (4), further comprising an acid generator comprising at least one onium salt selected from the group consisting of;

a triphenylsulfonium salt represented by the following formula (IIa)

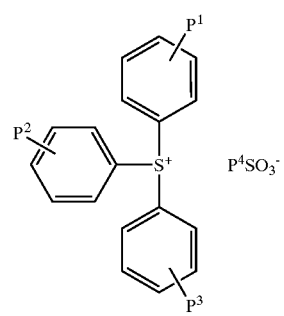

wherein $P^1$, $P^2$ and $P^3$ each independently represent hydrogen, hydroxy, alkyl having 1 to 6 carbon atoms, or alkoxy having 1 to 6 carbon atoms and $P^4SO_3^-$ represents an organic sulfonate ion;

a diphenyliodonium salt represented by the following formula (IIb)

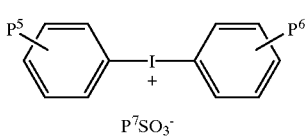

(IIb)

wherein $P^5$ and $P^6$ each independently represent hydrogen, hydroxy, alkyl having 1 to 6 carbon atoms, or alkoxy having 1 to 6 carbon atoms and $P^7SO_3^-$ represents an organic sulfonate ion; and a sulfonium salt represented by the following formula (IIc)

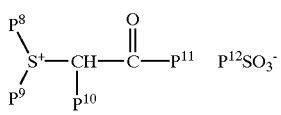

(IIc)

wherein $P^8$ and $P^9$ each independently represent alkyl having 1 to 6 carbon atoms or cycloalkyl having 3 to 10 carbon atoms, or when $P^8$ and $P^9$ are combined with $S^+$ to form a ring, $P^8$ and $P^9$ together with $S^+$ represent an alicyclic hydrocarbon group having 3 to 7 carbon atoms; at least one —$CH_2$— group of the alicyclic hydrocarbon group may be substituted with a —CO— group and at least one —$CH_2$— group of the alicyclic hydrocarbon group may be substituted with oxygen or sulfur; $P^{10}$ represents a hydrogen and $P^{11}$ represents alkyl having 1 to 6 carbon atoms, cycloalkyl having 3 to 10 carbon atoms, or an aromatic ring group which may be substituted, or when $P^{10}$ and $P^{11}$ are combined with an adjacent CHC(O) group to form a ring, $P^{10}$ and $P^{11}$ together with the CHC(O) group represent 2-oxocycloalkyl; and $P^{12}SO_3^-$ represents an organic sulfonate ion.

(6) The composition according to (5), wherein $Q^5$ and $Q^6$ in the formula (I) each independently represent perfluoroalkyl having 1 to 8 carbon atoms; and $p^4$ in the formula (IIa), $P^7$ in the formula (IIb) and $P^{12}$ in the formula (IIc) each independently represent perfluoroalkyl having 1 to 8 carbon atoms, alkyl having 1 to 8 carbon atoms, an aromatic group having 6 to 12 carbon atoms, or a camphor group.

(7) The composition according to (5) or (6), wherein the weight ratio of the sulfonium salt represented by the formula (I) to the at least one onium salt selected from the group consisting of the triphenylsulfonium salt represented by the formula (IIa), the diphenyliodonium salt represented by the formula (IIb) and the sulfonium salt represented by the formula (IIc) is 9:1 to 1:9.

(8) The composition according to any one of (4) to (7), wherein the content of the structural unit having a group that is unstable to acid in the resin is 10 to 80 mol %.

(9) The composition according to any one of (4) to (8), wherein the structural unit having a group that is unstable to acid in the resin is 2-alkyl-2-adamantyl (meth)acrylate or 1-(1-adamantyl)-1-alkylalkyl (meth)acrylate.

(10) The composition according to (9), wherein the resin further comprises at least one structural unit selected from the group consisting of: a structural unit derived from p-hydroxystyrene; a structural unit derived from m-hydroxystyrene; a structural unit derived from 3-hydroxy-1-adamantyl (meth)acrylate; a structural unit derived from 3,5-dihydroxy-1-adamantyl (meth)acrylate; a structural unit derived from (meth)acryloyloxy-γ-butyrolactone wherein at least one hydrogen on the lactone ring may be substituted by alkyl; and a structural unit represented by the following formulae (IIIa) and (IIIb)

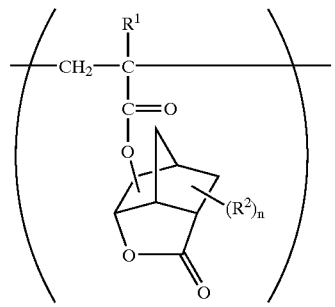

(IIIa)

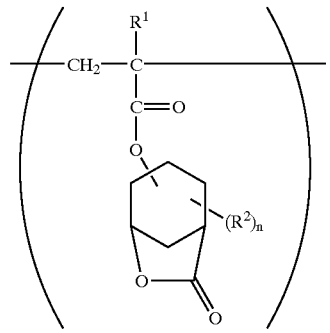

(IIIb)

wherein $R^1$ and $R^2$ each independently represent hydrogen, methyl, or trifluoromethyl and n represents an integer from 1 to 3.

(11) The composition according to (9) to (10), wherein the resin further comprises a structural unit derived from 2-norbornene and a structural unit derived from aliphatic unsaturated dicarboxylic anhydride.

(12) The composition according to any one of (4) to (11), further comprising an amine as a quencher.

(13) The composition according to any one of (4), further comprising a surfactant.

Further, the present invention is directed to: (14) A polymerization initiator composition comprising the present sulfonium salt and a sensitizer (hereinafter referred to as "the present polymerization initiator composition").

DESCRIPTION OF EMBODIMENT

In the present sulfonium salt, $Q^1$, $Q^2$ and $Q^3$ each independently represent hydrogen, hydroxy, alkyl having 1 to 6 carbon atoms, or alkoxy having 1 to 6 carbon atoms, wherein each of the alkyl and the alkoxy may be a straight or branched chain. However, the case where all of $Q^1$, $Q^2$ and $Q^3$ are the same is excluded. That is, two of them can be the same. Examples of such alkyl include methyl, ethyl, propyl, isopropyl, butyl, tert-butyl, pentyl, and hexyl. Specific examples of such alkoxy include methoxy, ethoxy, propoxy, and butoxy.

In the formula (I), $Q^4$ and $Q^5$ each independently represent perfluoroalkyl having 1 to 8 carbon atoms. Examples of such perfluoroalkyl include trifluoromethyl, perfluoroethyl, perfluorobutyl, and perfluorooctyl, The present sulfonium salt can be prepared according to a known method. For example, it may be prepared according to the following reaction scheme:

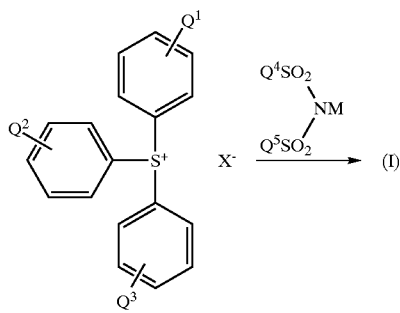

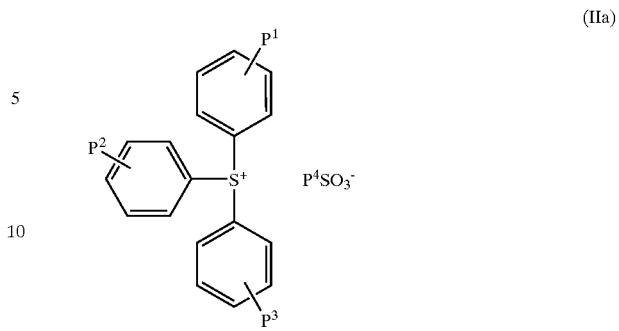

wherein $Q^1$, $Q^2$, $Q^3$, $Q^4$ and $Q^5$ are as defined above; X represents a halogen such as bromine, iodine and the like; and M represents an alkali metal such as sodium, lithium, potassium and the like or hydrogen.

Specific examples of the present sulfonium salt include the following compounds: 4-methylphenyldiphenylsulfonium trifluoro-N-[(trifluoromethyl)sulfonyl]methanesulfonamidate, 4-tert-butylphenyldiphenylsulfonium trifluoro-N-[(trifluoromethyl)sulfonyl]methanesulfonamidate, 4-hydroxyphenyldiphenylsulfonium trifluoro-N-[(trifluoromethyl)sulfonyl]methanesulfonamidate, 4-methoxylphenyldiphenylsulfonium trifluoro-N-[(trifluoromethyl)sulfonyl]methanesulfonamidate, 4-methylphenyldiphenylsulfonium perfluoro-N-[(perfluoroethyl)sulfonyl]-1-ethanesulfonamidate, 4-tert-butylphenyldiphenylsulfonium perfluoro-N-[(trifluoroethyl)sulfonyl]-1-ethanesulfonamidate, 4-hydroxyphenyldiphenylsulfonium perfluoro-N-[(perfluoroethyl)sulfonyl]-1-ethanesulfonamidate, 4-methoxyphenyldiphenylsulfonium perfluoro-N-[(perfluoroethyl)sulfonyl]-1-ethanesulfonamidate, 4-methylphenyldiphenylsulfonium perfluoro-N-[(perfluorobutyl)sulfonyl]-1-butanesulfonamidate, 4-tert-butylphenyldiphenylsulfonium perfluoro-N-[(perfluorobutyl)sultonyl]-1-butanesulfonamidate, 4-hydroxyphenyldiphenylsulfonium perfluoro-N-[(perfluorobutyl)sulfonyl]-1-butanesulfonamidate, 4-methoxylphenyldiphenylsulfonium perfluoro-N-[(perfluorobutyl)sulfonyl]-1-butanesulfonamidate, 4-methylphenyldiphenylsulfonium trifluoro-N-[(perfluorobutyl)sulfonyl]methanesulfonamidate, 4-tert-butylphenyldiphenylsulfonium trifluoro-N-[(perfluorobutyl)sulfonyl]methanesulfonamidate, 4-hydroxyphenyldiphenylsulfonium trifluoro-N-[(perfluorobutyl)sulfonyl]methanesulfonamidate, 4-methoxylphenyldiphenylsulfonium trifluoro-N-[(perfluorobutyl)sulfonyl]methanesulfonamidate, and the like.

Next, description will be made of the present resist composition.

The present resist composition comprises: a resin which contains a structural unit having a group unstable to an acid and which is insoluble or slightly soluble by itself in an aqueous alkali, but becomes soluble in the aqueous alkali by an action of the acid; and the present sulfonium salt.

Preferably, the present resist composition further comprises an acid generator comprising at least one onium salt selected from the group consisting of a triphenylsulfonium salt represented by the following formula (IIa), a diphenyliodonium salt represented by the following formula (IIb), and a sulfonium salt represented by the following formula (IIc).

wherein $P^1$, $P^2$ and $P^3$ each independently represent hydrogen, hydroxy, alkyl having 1 to 6 carbon atoms, or alkoxy having 1 to 6 carbon atoms and $P^4SO_3^-$ represents an organic sulfonate ion.

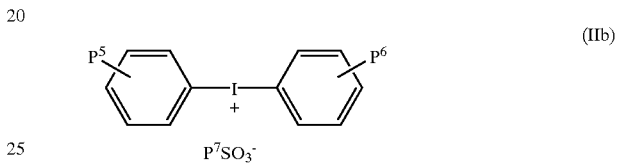

wherein $P^5$ and $P^6$ each independently represent hydrogen, hydroxy, alkyl having 1 to 6 carbon atoms, or alkoxy having 1 to 6 carbon atoms and $P^7SO_3^-$ represents an organic sulfonate ion.

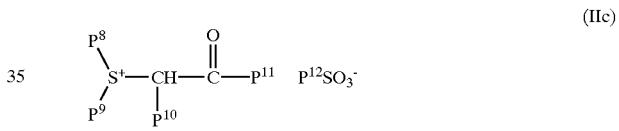

wherein $P^8$ and $P^9$ each independently represent alkyl having 1 to 6 carbon atoms or cycloalkyl having 3 to 10 carbon atoms, or when $P^8$ and $P^9$ are combined with $S^+$ to form a ring, $P^8$ and $P^9$ together with $S^+$ represent an alicyclic hydrocarbon group having 3 to 7 carbon atoms; at least one —CH$_2$— group of the alicyclic hydrocarbon group may be substituted with a —CO— group and at least one —CH$_2$— group of the alicyclic hydrocarbon group may be substituted with oxygen or sulfur; $P^{10}$ represents a hydrogen and $P^{11}$ represents alkyl having 1 to 6 carbon atoms, cycloalkyl having 3 to 10 carbon atoms, or an aromatic ring group which may be substituted, or when $P^{10}$ and $P^{11}$ are combined with an adjacent CHC(O) group to form a ring, $P^{10}$ and $P^{11}$ together with the CHC(O) group represent 2-oxocycloalkyl; and $P^{12}SO_3^-$ represents an organic sulfonate ion.

An acid generator for use in the present resist compositions is a substance which is decomposed to produce an acid when the substance itself or a resist composition containing the substance is subjected to the action of a radiation such as light, electron beam and the like. The present resist composition contains the present sulfonium salt used either alone or in combination with the present onium salt.

In the formulae (IIa), (IIb) and (IIc) related to the present onium salt, $P^1$, $P^2$, $P^3$, $P^5$ and $P^6$ each independently represent hydrogen, hydroxy, alkyl having 1 to 6 carbon atoms, or alkoxy having 1 to 6 carbon atoms, wherein each of the alkyl and the alkoxy may be a straight or branched chain.

Specific examples of such alkyl include methyl, ethyl, propyl, isopropyl, butyl, tert-butyl, pentyl, and hexyl. Specific examples of such alkoxy include methoxy, ethoxy, propoxy, and butoxy.

In the formula (IIc), $P^8$ and $P^9$ each independently represent alkyl having 1 to 6 carbon atoms or cycloalkyl having 3 to 10 carbon atoms, or when $P^8$, $P^9$ and $S^+$ are combined together to form a ring, they represent an alicyclic hydrocarbon group having 3 to 7 carbon atoms. At least one —$CH_2$— group of the alicyclic hydrocarbon group may be substituted with a —CO— group and at least one —$CH_2$— group of the alicyclic hydrocarbon group may be substituted with oxygen or sulfur.

$P^{10}$ represents hydrogen and $P^{11}$ represents alkyl having 1 to 6 carbon atoms, cycloalkyl having 3 to 10 carbon atoms, or an aromatic ring group which may be substituted, or when $P^{10}$ and $P^{11}$ are combined with an adjacent CHC(O) group to form a ring, $P^{10}$ and $P^{11}$ together with the CHC(O) group represent 2-oxocycloalkyl.

Specific examples of such alkyl include methyl, ethyl, propyl, isopropyl, butyl, tert-butyl, pentyl, and hexyl. Specific examples of such cycloalkyl include cyclopropyl, cyclobutyl, cyclopentyl, cyclohexyl, and cycloheptyl.

In the formulae (IIa), (IIb) and (IIc), $P^4SO_3^-$, $P^7SO_3^-$ and $P^{12}SO_3^-$ each forming an anion represent respective organic sulfonate ions. Here, each of $P^4$, $P^7$ and $P^{12}$ can independently be an organic group having 1 to about 12 carbon atoms, e.g. perfluoroalkyl having 1 to 8 carbon atoms, alkyl having 1 to 8 carbon atoms, an aromatic group having 6 to 12 carbon atoms, or a camphor group. Specific examples of such alkyl having 1 to 8 carbon atoms include a heptyl group and an octyl group in addition to the aforementioned specific examples of alkyl having 1 to 6 carbon atoms. Examples of such aromatic group having 6 to 12 carbon atoms include phenyl group, tolyl group, naphthyl group and the like. Specific examples of such perfluoroalkyl having 6 to 12 carbon atoms include those examples same as mentioned above.

The triphenylsulfonium salt of the formula (IIa), the diphenyliodonium salt of the formula (IIb) and the sulfonium salt of the formula (IIc) can be used as they are if they are commercially available products, or can be prepared according to the respective conventional procedures.

The triphenylsulfonium salt of the formula (IIa) can be prepared by methods including, for example: a method reacting a corresponding triphenylsulfonium bromide with a silver salt of a sulfonic acid having the same anion as in an intended compound; a method reacting a corresponding diphenyl sulfoxide, a benzene compound (e.g, benzene, toluene, aromatic compound, etc.) and perfluoroalkanesulfonic acid in the presence of trifluoroacetic acid anhydride according to the method described in Chem. Pharm. Bull., Vol. 29, 3753 (1981); and a method reacting corresponding aryl Grignard reagent with thionyl chloride and then reacting the reaction product with triorganosilyl halide to give triarylsulfonium halide, which in turn is allowed to react with a silver salt of a sulfonic acid having the same anion as in an intended compound, according to the method described in JP-A-H08-311018.

A compound of the formula (IIa) wherein $P^1$, $P^2$ and/or $P^3$ are/is hydroxy can be prepared by a method treating triphenylsulfonium salt having a tert-butyl group on a benzene ring with a sulfonic acid having the same anion as in the intended compound to eliminate the tert-butyl group according to the method described in JP-A-H08-311018.

The diphenyliodonium salt of the formula (IIb) can be prepared by methods including, for example: a method reacting iodyl sulfate and a corresponding aryl compound and then adding a sulfonic acid having the same anion as in an intended compound to the reaction product according to the teaching of J. Am. Chem. Soc., vol. 81, 342 (1959); a method wherein a reaction product resulting from addition of iodine and trifluoroacetic acid to a mixed solution of acetic anhydride and fuming nitric acid is allowed to react with a corresponding aryl compound, followed by addition of a sulfonic acid having the same anion as in an intended compound to the resulting product; and a method wherein concentrated sulfuric acid is added dropwise to a mixture of a corresponding aryl compound, acetic anhydride and potassium iodate to cause a reaction, followed by addition of a sulfonic acid having the same anion as in an intended compound to the resulting reaction product according to the method described in JP-A-H09-179302.

The sulfonium salt of the formula (IIc) can be prepared by, for example, a method reacting α-halogenoketone with sulfide compound to produce a sulfonium halide and further reacting a corresponding sulfonic acid or a metal salt thereof with the resulting sulfonium halide, which is taught by J. V. Crivello et al., J. Polymer Sicience., Polymer Chemistry Edition, Vol. 17 2877–2892 (1979).

Specific examples of triphenylsulfonium salts, diphenyliodoniun salts and sulfonium salts within the definitions of the respective formulae (IIa), (IIb) and (IIc) include the following compounds: triphenylsulfonium methanesulfonate, triphenylsulfonium ethanesulfonate, triphenylsulfonium trifluoromethanesulfonate, triphenylsultonium perfluorobutanesulfonate, triphenylsulfonium p-toluenesulfonate, triphenylsulfonium camphorsulfonate, 4-methylphenyldiphenylsulfonium methanesulfonate, 4-methylphenyldiphenylsulfonium ethanesulfonate, 4-methylphenyldiphenylsulfonium trifluoromethanesulfonate, 4-methylphenyldiphenylsulfonium benzenesulfonate, 4-methylphenyldiphenylsulfonium perfluorobutanesulfonate, 4-methylphenyldiphenylsulfonium p-toluenesulfonate, 4-methylphenyldiphenylsulfonium camphorsulfonate, 4-hydroxyphenyldiphenylsulfonium trifluoromethanesulfonate, 4-methoxyphenyldiphenylsulfonium trifluoromethanesulfonate, tris(4-methylphenyl)sulfonium trifluoromethanesulfonate, tris(4-methoxyphenyl)sulfonium trifluoromethanesulfonate, 4-hydroxyphenyldiphenylsulfonium p-toluenesulfonate, 4-methoxyphenyldiphenylsulfonium perfluorobutanesulfonate, tris(4-methylphenyl)sulfonium perfluorobutanesulfonate, tris(4-methoxyphenyl)sulfonium perfluorobutanesulfonate, diphenyliodonium perfluorobutanesulfonate, di(4-methoxyphenyl) iodonium perfluorobutanesulfonate, di (4-tert-butylphenyl)iodonium perfluorobutanesulfonate, di(4-tert-butylphenyl)iodonium methanesulfonate, di(4-tert-butylphenyl)iodonium ethanesulfonate, di(4-tert-butylphenyl)iodonium trifluoromethanesulfonate, di(4-tert-butylphenyl)iodonium benzenesulfonate, di(4-tert-butylphenyl) iodonium 2,4,6-triisopropylbenzenesulfonate, di(4-tert-butylphenyl) iodoniun camphorsulfonate, and the like. 3,3-dimethyl-2-oxobutyldibutylsulfonium trifluoromethanesulfonate, 3,3-dimethyl-2-oxobutylthiacyclopentanium trifluoromethanesulfonate, 2-phenyl-2-oxoethylthiacyclopentanium perfluorobutanesulfonate, and 2-naphthyl-2-oxoethylthiacyclopentanium perfluorobutanesulfonate, and the like.

Next, description will be made of the resin component forming part of the present resist composition. The resin contains a structural unit having a group that is unstable to acid. Resins for use in chemical amplifying type positive resists are of the type which, per se, is insoluble or slightly soluble in an alkali, but which has some groups that can be dissociated by an action of acid and, therefore, becomes soluble in the alkali after the dissociation. The group that is unstable to acid in the present invention can be any one of various such known groups.

A specific example of the group that is unstable to acid is —COOR group. Examples of R include alkyl, 1-alkoxyalkyl, 1-(alkoxyalkoxy) alkyl, 1-(alkylcarbonyloxyalkoxy)alkyl, 1-(cycloalkyloxyalkoxy) alkyl, 1-(cycloalkylcarbonyloxyalkoxy) alkyl, tetrahydrofuryl, tetrahydropyranyl, isobornyl, cycloalkyl, cycloalkylalkyl and the like. There can be mentioned, for example, alkyloxycarbonyl such as methoxycarbonyl and tert-butoxycarbonyl; acetal type oxycarbonyl such as methoxymethoxycarbonyl, ethoxymethoxycarbonyl, 1-ethoxyethoxycarbonyl, 1-isobutoxyethoxycarbonyl, 1-isopropoxyethoxycarbonyl, 1-ethoxypropoxycarbonyl, 1-(2-methoxyethoxy)ethoxycarbonyl, 1-(2-acetoxyethoxy) ethoxycarbonyl, 1-[2-(1-adamantyloxy)ethoxy] ethoxycarbonyl, 1-[2-(1-adamantanecarbonyloxy) ethoxy] ethoxycarbonyl, tetrahydro-2-furyloxycarbonyl, tetrahydro-2-pyranyloxycarbonyl and the like; isobornyloxycarbonyl; and alicyclic oxycarbonyl such as 2-alkyl-2-adamantyloxycarbonyl, 1-(1-adamantyl)-1-alkylalkyloxycarbonyl and the like. Monomers that can lead to the formation of a structural unit having such a —COOR group may be (meth)acrylic esters such as methacrylic ester and acrylic ester or monomers of the type having —COOR bonded to an alicyclic group, such as esters of norbornenecarboxylic acid, tricyclodecenecarboxylic acid and tetracyclodecenecarboxylic acid.

Among such monomers, those of the type having a bulky group including an alicyclic group such as 2-alkyl-2-adamantyl or 1-(1-adamantyl)-1-alkylalkyl for example as R of the —COOR are preferable because the use of such a monomer provides for a resist having superior resolution. Examples of such monomers having a bulky group include 2-alkyl-2-adamantyl (meth)acrylate, 1-(1-adamantyl)-1-alkylalkyl (meth)acrylate, 2-alkyl-2-adamantyl 5-norbonene-2-carboxylate, 1-(1-adamantyl)-1-alkylalkyl 5-norbornene-2-carboxylate and the like. Among others, use of 2-alkyl-2-adamantyl (meth)acrylate as the monomer to produce the resin containing a structural unit having a group that is unstable to acid is preferable because the resulting resist composition exhibits superior resolution. Representative examples of such 2-alkyl-2-adamantyl (meth)acrylates include 2-methyl-2-adamantyl acrylate, 2-methyl-2-adamantyl methacrylate, 2-ethyl-2-adamantyl acrylate, 2-ethyl-2-adamantyl methacrylate, and 2-n-butyl-2-adamantyl acrylate. Among them, 2-ethyl-2-adamantyl (meth)acrylate is particularly preferable because the use thereof provides for a resist having sensitivity and heat resistance in good balance. Of course, such a monomer may be used in combination with other monomer(s) having a group that can be dissociated by the action of acid.

Usually, such a 2-alkyl-2-adamantyl (meth)acrylate can be prepared by the reaction of 2-alkyl-2-adamantanol or a metal salt thereof with an acrylic or methacrylic halide.

The resin used in the present invention may further contain other structural unit(s) which is not dissociable or is slightly dissociable by the action of acid, in addition to the aforementioned structural unit having a group that is unstable to acid. Examples of other structural units which can be contained in the resin include a structural unit derived from a monomer having a free carboxylic acid group such as acrylic acid, methacrylic acid, and the like; a structural unit derived from an aliphatic unsaturated dicarboxylic anhydride such as maleic anhydride, itaconic anhydride and the like; a structural unit derived from 2-norbornene; a structural unit derived from (meth)acrylonitrile; and structural units derived from various (meth)acrylic esters.

The resin may contain a structural unit derived from hydroxystyrene if the intended resist is to be subjected to KrF exposure because a light absorption problem will not arise, though this structural unit is not preferable if the intended resist is to be subjected to ArF exposure because light absorption increases undesirably.

In view of the adhesitivity of resist to a substrate, particularly preferable for use in the resin of the present invention are; a structural unit derived from p-hydroxystyrene; a structural unit derived from m-hydroxystyrene, a structural unit derived from 3-hydroxy-1-adamantyl (meth)acrylate, a structural unit derived from 3,5-dihydroxy-1-adamantyl (meth)acrylate, a structural unit derived from (meth)acryloyloxy-γ-butyrolactone wherein one or more hydrogen on the lactone ring may be substituted by alkyl; and a structural unit obtained by copolymerization of alicyclic lactones represented by the following respective formulae (IIIa) and (IIIb):

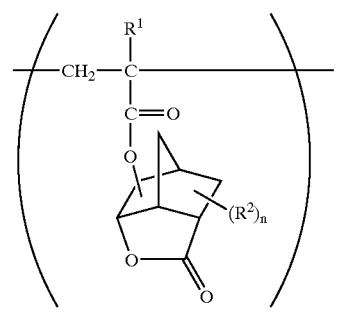

(IIIa)

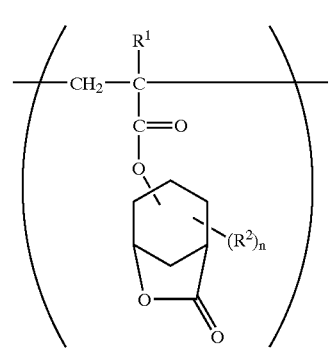

(IIIb)

wherein $R^1$ and $R^2$ each independently represent hydrogen, methyl, or trifluoromethyl and n represents an integer from 1 to 3.

While 3-hydroxy-1-adamantyl (meth)acrylate and 3,5-dihydroxy-1-adamantyl (meth)acrylate are commercially available, each of them can be prepared by reacting a corresponding hydroxyadamantane with a (meth)acrylic acid or a halide thereof. (Meth)acryloyloxy-γ-butyrolactone can be prepared by reacting acrylic acid or methacrylic acid with α- or β-bromo-γ-butyrolactone wherein one or more hydrogen on the lactone ring may be substituted with alkyl, or reacting acrylic halide or methacrylic halide with α- or β-hydroxy-γ-butyrolactone wherein one or more hydrogen on the lactone ring may be substituted with alkyl. Specific examples of monomers leading to the formation of a structural unit derived from the alicyclic lactone of the formula (IIIa) or (IIIb) include (meth)acrylic esters of alicyclic lactones having the following hydroxyl groups, and mixtures thereof. Each of these esters can be prepared by, for example, the reaction of a corresponding alicyclic lactone having hydroxyl group and a (meth)acrylic acid (Refer to JP-A-2000-26446 for example.).

merization of styrene and corresponding (meth)acrylic ester monomer and acetoxystyrene, followed by deacetylation with acid.

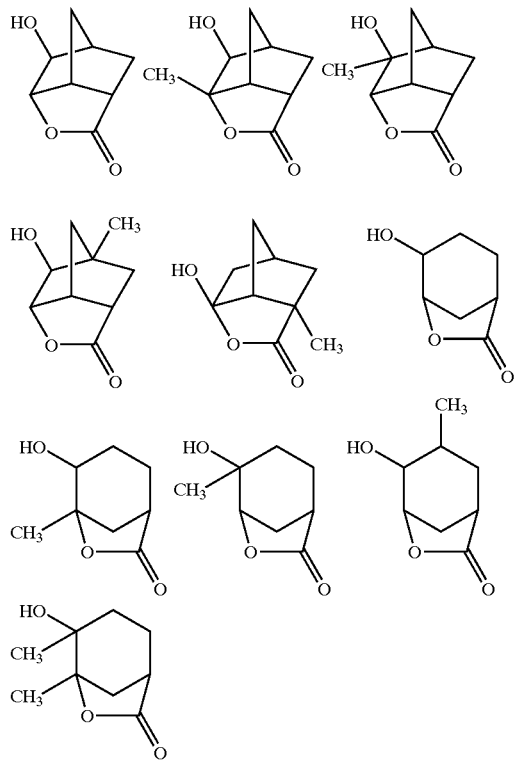

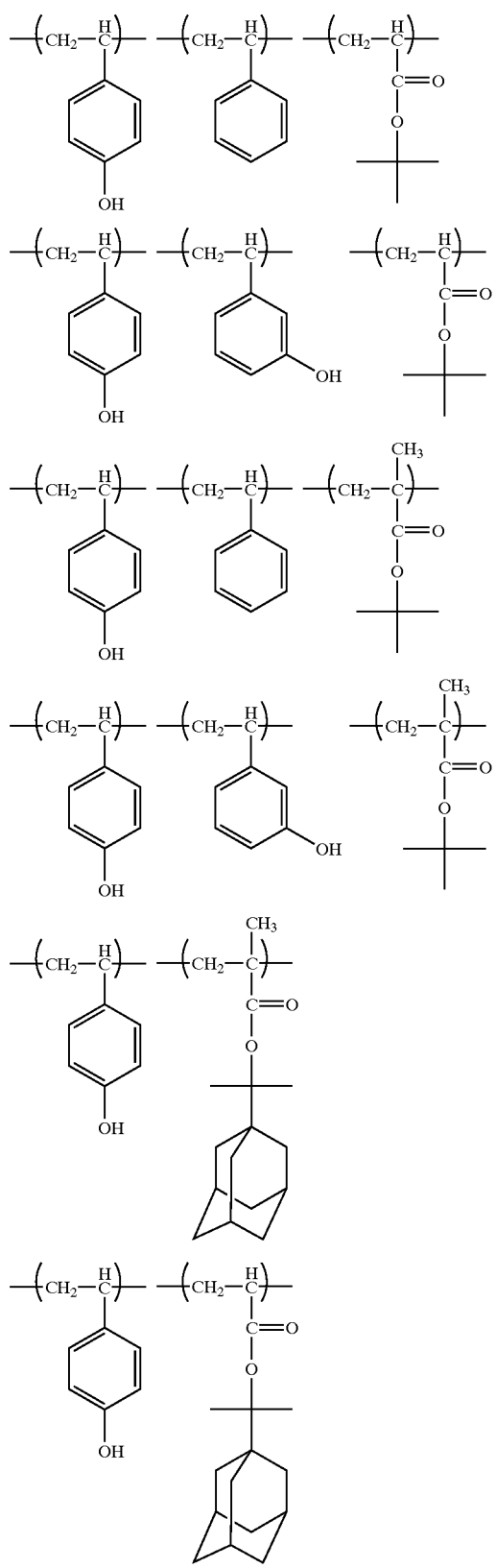

Any one of the structural unit derived from 3-hydroxy-1-adamantyl (meth)acrylate, structural unit derived from 3,5-dihydroxy-1-adamantyl (meth)acrylate, structural unit derived from α-(meth)acryloyloxy-γ-butyrolactone, structural unit derived from β-(meth)acryloyloxy-γ-butyrolactone and structural unit derived from alicyclic lactone represented by the formula (IIIa) or (IIIb), has high polarity and, hence, incorporation of any one of the structural units in the resin improves the adhesivity of a resist containing the resin to a substrate. Further, these structural units each contribute to an improvement in the resolution of resist.

Examples of such monomers leading to the formation of the structural unit derived from (meth)acryloyloxy-γ-butyrolactone include α-acryloyloxy-γ-butyrolactone, α-methacryloyloxy-γ-butyrolactone, α-acryloyloxy-β, β-dimethyl-γ-butyrolactone, α-methacryloyloxy-β, β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone, and β-methacryloyloxy-α-methyl-γ-butyrolactone.

In the case of KrF excimer laser exposure, the use of the structural unit derived from hydroxystyrene as the structural unit of the resin can provide for a resist having sufficient transmissivity. Specifically, the following p- or m-hydroxystyrene copolymer resins can be mentioned. Each of such copolymer resins can be obtained by radical poly-

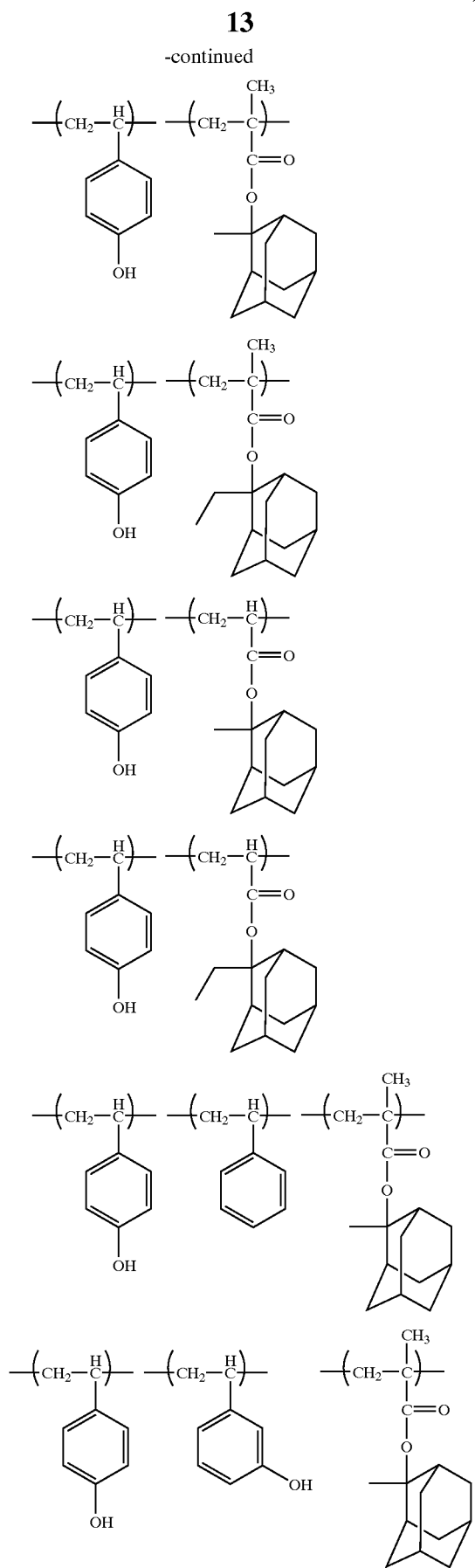
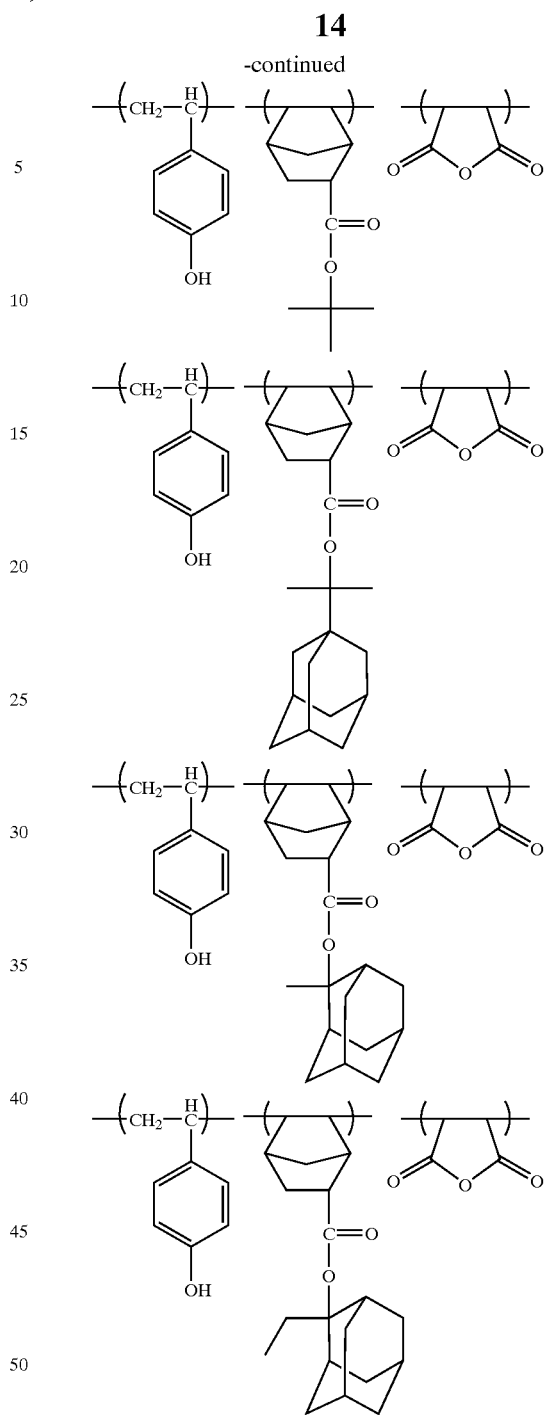

In the case of these copolymer resins, the use of 2-alkyl-2-adamantyl or 1-(1-adamantyl)-1-alkylalkyl as the group that is unstable to acid is more advantageous in terms of the dry etching resistance of the present resist composition.

A resin containing a structural unit derived from 2-norbornene is of a sturdy structure by virtue of its main chain directly having an alicyclic group and hence exhibits superior dry etching resistance. The structural unit derived from 2-norbornene can be introduced into the main chain by radical polymerization using, for example, a corresponding 2-norbornene and an aliphatic unsaturated dicarboxylic anhydride such as maleic anhydride or itaconic anhydride in combination. Accordingly, the structural unit derived from 2-norbonene is formed with its double bond open and is represented by the formula (IV) below. A structural unit derived from maleic anhydride and a structural unit derived from itaconic anhydride, which are structural units derived from respective aliphatic unsaturated dicarboxylic anhydrides, are formed with their respective double bonds open and are represented by the formulae (V) and (VI), respectively.

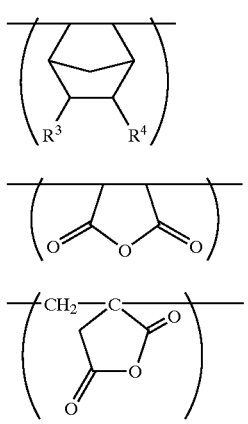

Here, $R^3$ and $R^4$ each independently represent hydrogen, alkyl having 1 to 3 carbon atoms, hydroxyalkyl having 1 to 3 carbon atoms, carboxyl, cyano or group-COOZ (z is an alcohol residue), or $R^3$ and $R^4$ can be combined together to form a carboxylic anhydride residue represented by —C(=O)OC(=O)—. Specific examples of alkyl for $R^3$ and/or $R^4$ include methyl, ethyl, and propyl, and specific examples of hydroxyalkyl for $R^3$ and/or $R^4$ include hydroxymethyl and 2-hydroxyethyl. Group-COOZ for $R^3$ and/or $R^4$ is esterified carboxyl, and examples of alcohol residues for Z include alkyl having 1 to about 8 carbon atoms which may be substituted, 2-oxooxolane-3-yl or 2-oxooxolane-4-yl. Substituents for alkyl include hydroxyl groups and alicyclic hydrocarbon residues. Specific examples of —COOZ for $R^3$ and/or $R^4$ include methoxycarbonyl, ethoxycarbonyl, 2-hydroxyethoxycarbonyl, tert-butoxycarbonyl, 2-oxooxolane-3-yloxycarbonyl, 2-oxooxolane-4-yloxycarbonyl, 1,1,2-trimethylpropoxycarbonyl, 1-cyclohexyl-1-methylethoxycarbonyl, 1-(4-methylcyclohexyl)-1-methylethoxycarbonyl, and 1-(1-adamantyl)-1-methylethoxycarbonyl.

Specific examples of monomers leading to the formation of the structural unit derived from 2-norbornene represented by the formula (IV) include the following compounds: 2-norbornene, 2-hydroxy-5-norbornene, 5-norbornene-2-carboxylate, methyl 5-norbornene-2-carboxylate, t-butyl 5-norbornene-2-carboxylate, 1-cyclohexyl-1-methylethyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl)ethyl 5-norbornene-2-carboxylate, 1-(1-adamantyl)-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 2-hydroxy-1-ethyl 5-norbornene-2-carboxylate, 5-norbornene-2-methanol, 5-norbornene-2,3-dicarboxylic anhydride and the like.

Generally, the resin used in the present invention preferably contains the structural unit having a group that is unstable to acid in an amount ranging from 10 to 80 mol %, though this range varies depending on the kind of radiation to be used for patterning exposure, the kind of group that is unstable to acid, and the like. Particularly where the structural unit derived from 2-alkyl-2-adatantyl (meth)acrylate or 1-(1-adamantyl)-1-alkylalkyl (meth)acrylate is used as the group that is unstable to acid, it is advantageous that the proportion of this structural unit is adjusted to 15 mol % or more relative to the overall amount of the resin. When the structural unit having a group that is unstable to acid is contained in the resin as coexisting with other structural unit(s) which is(are) hard to dissociate by the action of acid, such as the structural unit derived from 3-hydroxy-1-adamantyl (meth)acrylate, structural unit derived from 3,5-dihydroxy-1-adamantyl (meth)acrylate, structural unit derived from α-(meth)acryloyloxy-γ-butyrolactone, structural unit derived from β-(meth)acryloyloxy-γ-butyrolactone, structural unit derived from alicyclic lactone represented by the formula (IIIa) or (IIIb), structural unit derived from hydroxystyrene, structural unit derived from 2-norbornene represented by the formula (IV), or structural unit derived from maleic anhydride represented by the formula (V) or from itaconic anhydride represented by the formula (VI), which is the structural unit derived from an aliphatic unsaturated dicarboxylic anhydride, the total amount of these units is preferably adjusted to fall within the range of 20 to 90 mol % relative to the overall amount of the resin.

In the case where a 2-norbornene and an aliphatic unsaturated dicarboxylic anhydride are used as monomers to be copolymerized, these are preferably used in excess, taking into consideration the fact that they tend to exhibit low polymerzability.

By incorporating a basic compound, particularly a basic nitrogen-containing organic compound such as an amine for example, as a quencher into the present resist composition, performance deterioration caused by inactivation of acid which occurs due to post exposure delay can be diminished. Specific examples of basic compounds for use as the quencher include those represented by the following formulae.

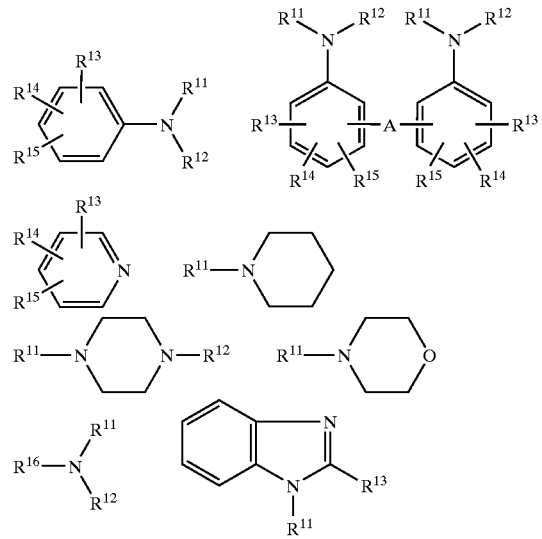

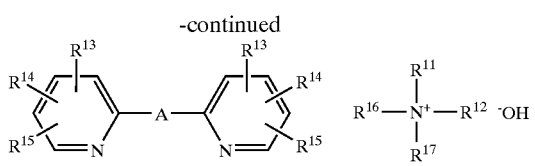

In the formulae noted above, $R^{11}$, $R^{12}$ and $R^{17}$ each independently represent hydrogen, alkyl, cycloalkyl or aryl. Each of the alkyl, cycloalkyl and aryl may independently be substituted with a hydroxyl group, amino group, or alkoxy group having 1 to 6 carbon atoms. The amino group may be substituted with an alkyl group having 1 to 4 carbon atoms. The alkyl preferably has about 1 to about 6 carbon atoms; the cycloalkyl preferably has about 5 to about 10 carbon atoms; and the aryl preferably has about 6 to about 10 carbon atoms.

$R^{13}$, $R^{14}$ and $R^{15}$ each independently represent hydrogen, alkyl, cycloalkyl, aryl, or alkoxy. Each of the alkyl, cycloalkyl, aryl and alkoxy may independently be substituted with a hydroxyl group, amino group, or alkoxy group having 1 to 6 carbon atoms. The amino group may be substituted with an alkyl group having 1 to 4 carbon atoms. The alkyl preferably has about 1 to about 6 carbon atoms; the cycloalkyl preferably has about 5 to about 10 carbon atoms; the aryl preferably has about 6 to about 10 carbon atoms; and the alkoxy preferably has about 1 to about 6 carbon atoms.

$R^{16}$ represents alkyl or cycloalkyl. Each of the alkyl and the cycloalkyl may independently be substituted with a hydroxyl group, amino group, or alkoxy group having 1 to 6 carbon atoms. The amino group may be substituted with an alkyl group having 1 to 4 carbon atoms. The alkyl preferably has about 1 to about 6 carbon atoms, and the cycloalkyl preferably has about 5 to about 10 carbon atoms.

A represents alkylene, carbonyl, imino, sulfide or disulfide. The alkylene preferably has about 2 to about 6 carbon atoms.

Among $R^{11}$ to $R^{17}$, those which can take on both a straight-chain structure and a branched-chain structure may have either structure.

Examples of such basic compounds include hexylamine, heptylamine, octylamine, nonylamine, aniline, o-, m- or p-toluidine, 4-nitroaniline, 1- or 2-naphtylamine, ethylenediamine, tetramethylenediamine, examethylenediamine, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, N-metyldibutylamine, N-methyldipentylamine, N-methyldihexylamine, N-methyldicyclohexylamine, N-methyldiheptylamine, N-methyldioctylamine, N-methyldinonylamine, N-methyldidecylamine, N-ethyldibutylamine, N-ethyldipentylamine, N-ethyldihexylamine, N-ethyldiheptylamine, N-ethyldioctylamine, N-ethyldinonylamine, N-ethyldidecylamine, N-methyldicyclohexylamine, tris[2-(2-methoxyethoxy)ethyl]amine, triisopropanolamine, N,N-dimethyaniline, 2,6-isopropylaniline, imidazole, pyridine, 4-methylpyridine, 4-methylimidazole, bipyridine, 2,2'-dipyridylamine, di-2-pyridylketone, 1,2-di(2-pyridyl) ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridylsulfide, 4,4'-dipyridyldisulfide, 1,2-bis(4-pyridyl)ethylene, 2,2'-dipicolylamine, 3,3'-dipicolylamine, tetramethylammonium hydroxide, tetraisopropylammonium hydroxide, tetrabutylammonium hydroxide, tetra-n-hexylammonium hydroxide, tetra-n-octylammonium hydroxide, choline, and the like. Hindered amine compounds having piperidine structure as described in JP-A-H11-52575 can be applicable as a quencher.

Preferably, the present resist composition contains the resin in an amount of 80 to 99.9 wt % and the acid generator comprising the present sulfonium salt in an amount of 0.1 to 20 wt %, based on the total solid content of the composition. In the present invention, when the present sulfonium salt and the present oinium salt are used in combination as the acid generator, usually the weight ratio of the two is preferably about 9:1 to about 1:9, more preferably about 8:2 to about 2:8.

When a basic compound is used as the quencher, the present resist composition contains the basic compound in an amount preferably ranging from about 0.01 to about 1 wt %, based on the total solid content of the present resist composition. The present resist composition may further be incorporated with small amounts of additives such as a sensitizer, dissolution inhibitor, other resin, surfactant, stabilizer, and dye.

The present resist composition is usually in the form of a resist liquid composition in which the aforementioned ingredients are dissolved in a solvent, and the resist liquid composition is to be applied onto a substrate such as a silicon wafer by a conventional process such as spin coating. The solvent used here is sufficient to dissolve the aforementioned ingredients, have an adequate drying rate, and give a uniform and smooth coat after evaporation of the solvent and, hence, solvents generally used in the art can be used. Examples of such solvents include glycol ether esters such as ethyl cellosolve acetate, methyl cellosolve acetate, and proplylene glycol monoethyl ether acetate; esters such as ethyl lactate, butyl acetate, amyl acetate, and ethyl pyruvate; ketones such as acetone, methyl isobutyl ketone, 2-heptanone, and cyclohexanone; and cyclic esters such as γ-butyrolactone. These solvents can be used either alone or in combination of at least two of them.

A resist film applied onto the substrate and then dried is subjected to exposure for patterning, then heat-treated for facilitating a deblocking reaction, and thereafter developed with an alkali developer. The alkali developer used here may be any one of various alkaline aqueous solutions used in the art; however, an aqueous solution of tetramethylammonium hydroxide or (2-hydroxyethyl)trimethylammonium hydroxide (commonly known as "choline") is often used.

A polymerization initiator composition comprising the present sulfonium salt and sensitizer can be used as polymerization initiator of cation polymerizable compound(s).

The polymerization initiator composition usually consists essentially of the present sulfonium salt and the sensitizer. Other component(s) such as can be incorporated as long as the initiating effect of the composition is not prevented.

In this specification, sensitizer means any compound promoting photo reaction of the present sulfonium salt.

Such sensitizer includes, for example, a compound readily releasing hydrogen radicals, radical polymerization inhibitor, a compound which reacts with sulfonium salt in the course of photo reaction of sulfonium salt and which releases protons as the result of the reaction, electron donor, and the like.

Specific examples of such sensitizer are anthraquinone derivatives such as phenotiazine, 2-ethylanthraquinone, and the like; 9,10-dialkoxyanthracene derivatives such as 9,10-dimethoxyanthracene, 9,10-diethoxyanthracene, 2-ethyl-9,10-dimethoxyanthracene, and the like; thioxanthone derivatives such as thioxanthone, isopropylthioxanthone, 2,4-dimethylthioxanthone, 2,4-diethylthioxanthone, 2,4-diisopropylthioxanthone, 2-chlorothioxanthone, and the like; carbazol derivatives such as N-ethylcarbazol, and the like; naphthalene derivatives having at least one hydroxy group or alkoxy group such as 1-naphthol, 2-methoxynaphthol, and the like.

In the polymerization initiator composition of the present invention, content of sensitizer is usually from 0.005 to 10 parts, preferably from 0.01 to 5 parts per 10 parts of the present sulfonium salt.

Cationic polymerizable compound means monomer which is addition polymerizable and whose extendable chain is cation such as carbonium ion, oxonium ion, and the like. Examples of such compounds include vinyl compounds, cycloalkane compounds, cyclic ether compounds, lactone compounds, aldehyde compounds, and the like.

The polymerization initiator composition of the present invention is stable and can be used in the same manner as conventional cationic polymerization initiators.

The present invention will be described more specifically by way of examples, which are not construed to limit the scope of the present invention. The "%" and "part(s)" used to represent the content of any component and the amount of any material used in the following examples are on a weight basis unless otherwise specifically noted. The weight-average molecular weight of any material used in the following examples is a value found by gel permeation chromatography using styrene as a standard reference material.

Acid Generator Synthesis 1: Synthesis of Acid Generator B1

A flask was charged with 7.58 parts of diphenyl sulfoxide, 15 parts of perfluoroethanesulfonimide and 75.81 parts of toluene, and then 15.74 parts of trifluoroacetic anhydride was added dropwise to the resulting mixture, followed by stirring at room temperature for 16 hours. The resulting mixture was separated into fractions, the toluene layer of which was then discarded, and 113.71 parts of chloroform was added to the remainder. The resulting mixture was washed by adding 56.86 parts of ion-exchanged water thereto. This washing procedure was repeated 10 times, and the resulting organic layer was concentrated to give 1.9 parts of an object. It was confirmed by means of NMR ("GX-270" manufactured by JEOL) that this compound was 4-methylphenyldiphenylsulfonium perfluoro-N-[(perfluoroethyl)sulfonyl]-1-ethanesulfonamidate represented by the following formula:

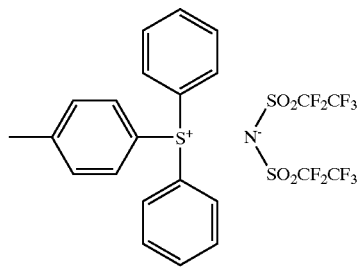

$^1$H-NMR (chloroform-d, internal standard: tetramethylsilane):

δ (ppm) 2.45 (s, 3H); 7.59–7.88 (m, 14H)
$^{19}$F-NMR (chloroform-d, external standard: hexafluorobenzene):

δ (ppm) −83.35 (s, 6F); −122.21 (S, 4F)

Acid Generator Synthesis 2: Synthesis of Acid Generator B2

A flask was charged with 20 parts of 4-tert-butylphenyldiphenylsulfonium iodate and 300 parts of methanol, and then a solution composed of 17.34 parts of perfluoroethanesulfonimde, 20 parts of ion-exchanged water and 20 parts of methanol was added dropwise to the resulting mixture. After stirring at room temperature, the resulting mixture was concentrated and then admixed with 500 parts of chloroform. The resulting mixture was added by 100 parts of ion-exchanged water, and then washed. Thereafter, the resulting organic layer was concentrated to give 26.89 parts of an object. It was confirmed by means of NMAR ("GX-270" manufactured by JEOL) that this compound was 4-tert-butylphenyldiphenylsulfonium perfluoro-N-[(perfluoroethyl)sulfonyl]-1-ethanesulfonamidate represented by the following formula:

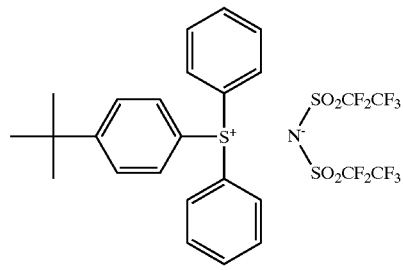

$^1$H-NMR (chloroform-d, internal standard: tetramethylsilane):

δ (ppm) 1.34 (s, 9H); 7.78–7.89 (m, 14H)
$^{19}$F-NMR (chloroform-d, external standard: hexafluorobenzene):

δ (ppm) −83.53 (s, 6F); −122.25 (s, 4F)

Acid Generator Synthesis 3: Synthesis of Acid Generator B3

A flask was charged with 2.23 parts of diphenyl sulfoxide, 5 parts of (trifluoromethanesulfone) perfluorobutanesulfonimide and 22.34 parts of toluene, and then 4.64 parts of trifluoroacetic anhydride was added dropwise to the resulting mixture, followed by stirring at room temperature. The resulting mixture was separated into fractions, the toluene layer of which was then discarded, and 160 parts of chloroform was added to the remainder. The resulting mixture was added by 40 parts of ion-exchanged water and washed. The resulting organic layer was then concentrated to give 5.65 parts of an object. It was confirmed by means of NMR ("GX-270" manufactured by JEOL) that this compound was 4-methylphenyldiphenylsulfonium trifluoro-N-[(perfluorobutane)sulfonyl]-1-methanesulfonamidate represented by the following formula:

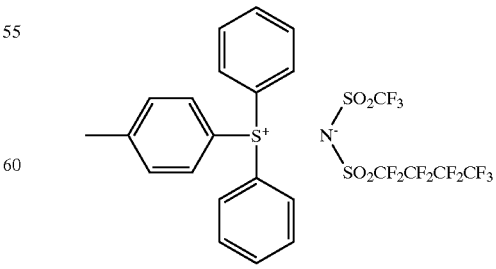

$^1$H-NMR (chloroform-d, internal standard: tetramethylsilane):

δ (ppm) 2.45 (s, 3H); 7.59–7.89 (m, 14H)

$^{19}$F-NMR (chloroform-d, external standard: hexafluorobenzene):

δ (ppm) −83.75 (s, 3F); −85.32 (s, 3F); −118.30 (s, 2F); −126.01 (s, 2F); −130.68 (s, 2F)

Resin Synthesis 1 (Synthesis of Resin 1)

Provided were 2-ethyl-2-adamantyl methacrylate, 3-hydroxy-1-adamantyl methacrylate and α-methacryloyloxy-γ-butyrolactone at a molar ratio of 5:2.5:2.5 (20.0 parts:9.5 parts:7.3 parts) and methyl isobutyl ketone weighing twice as large as the total weight of all the monomers was added to the mixture to give a solution. The solution was admixed with azobisisobutyronitrile as an initiator in an amount of 2 mol % relative to the total amount of all the monomers and then heated at 80° C. for about 8 hours. Thereafter, the operation of pouring the reaction solution into a large quantity of heptane was performed three times to purify the reaction solution. As a result, a copolymer having a weight-average molecular weight of about 9,200 was obtained. This copolymer, herein referred to as resin A1, contained units represented by the following respective formulae:

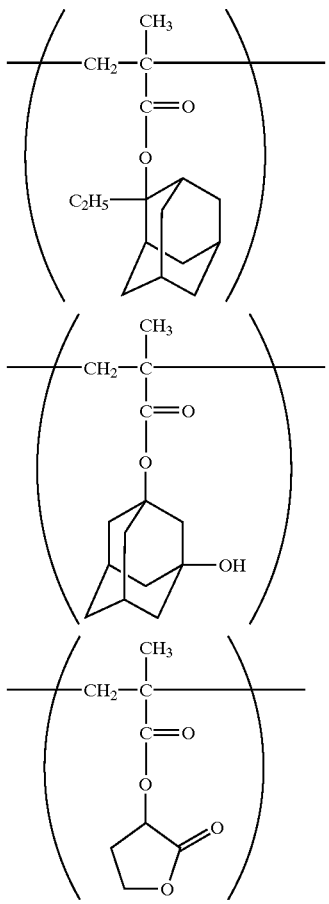

Resist compositions were prepared using the following materials as well as the resin obtained in the resin synthesis described above and then evaluated.

Acid Generators

B1: 4-methylphenyldiphenylsulfonium perfluoro-N-[(perfluoroethyl)sulfonyl]-1-ethanesulfonamidate B2: 4-tert-butylphenyldiphenylsulfonium perfluoro-N-[(perfluoroethyl)sulfonyl]-1-ethanesulfonamidate B3: 4-methylphenyldiphenylsulfonium trifluoro-N-[(perfluorobutane)sulfonyl]-1-methanesulfonamidate C1: 4-methylphenyldiphenylsulfonium perfluorooctanesulfonate C2: triphenylsulfonium perfluoro-N-[(perfluoroethyl)sulfonyl]-1-ethanesulfonamidate C3: tri-(4-tert-butylphenyl)sulfonium perfluoro-N-[(perfluoroethyl) sulfonyl]-1-ethanesulfonamidate Quencher D1: 2,6-diisopropylaniline Solvent E1: propylene glycol monomethyl ether acetate 57 parts
γ-butyrolactone 3 parts

EXAMPLE 1 AND COMPARATIVE EXAMPLE 1

The following ingredients were mixed together to give solutions, which in turn were filtered with a 0.2 μm pore size filter of fluororesin to prepare resist liquids.

Resin (the type and amount thereof shown in Table 1)

Acid generator (the type and amount thereof shown in Table 1)

Quencher (the type and amount thereof shown in Table 1)

Solvent (the type and amount thereof shown in Table 1)

Silicon wafers were each coated with "ARC-25-8", which is an organic anti-reflective coating composition available from Brewer Co., and then baked under the conditions: 215° C., 60 seconds, to form a 780 Å-thick organic anti-reflective coating. Each of the resist liquids prepared as above was spin-coated over the anti-reflective coating so that the thickness of the resulting film became 0.39 μm after drying. The silicon wafers thus coated with the respective resist liquids were each prebaked on a direct hotplate at 130° C. for 60 seconds. Using an ArF excimer stepper ("NSR ArF" manufactured by Nicon Corporation, NA=0.55, σ=0.6), each wafer thus formed with the respective resist film was subjected to line and space pattern exposure, with the exposure quantity being varied stepwise.

After the exposure, each wafer was subjected to post-exposure baking on a hotplate at 130° C. for 60 seconds and then to paddle development for 60 seconds with an aqueous solution of 2.38 wt % tetramethylammonium hydroxide.

A bright field pattern developed on the organic anti-reflective coating substrate was observed with a scanning electron microscope, the results of which are shown in Table 2. The term "bright field pattern", as used herein, means a pattern obtained by exposure and development through a reticle comprising an outer frame made of a chromium layer (light-shielding layer) and linear chromium layers (light-shielding layers) formed on a glass surface (light-transmitting portion) extending inside the outer frame. Thus, the bright field pattern is such that, after exposure and development, resist layer surrounding the line and space pattern is removed while resist layer corresponding to the outer frame is left on the outer side of the region from which the resist layer is removed.

Effective sensitivity is represented in such an exposure quantity that a 0.18 μm line and space pattern and a corresponding bright field pattern became 1:1.

Resolution is represented in a minimum measure of a line and space pattern at which a corresponding bright field pattern was separated with the exposure quantity of the effective sensitivity.

Cross-sectional views of resists are evaluated using symbols "◯", "X" and "Δ", which represent rectangular top configuration, rounded top configuration and T-top configuration, respectively, of resists formed with respective 0.1 μm line and space patterns at the exposure quantity of the effective sensitivity.

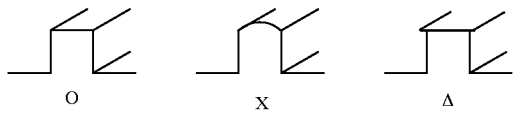

◯　　　　X　　　　Δ

TABLE 1

| Example No. | Resin | Acid Generator | Quencher | Solvent |
|---|---|---|---|---|
| Example 1 | A1/10 parts | B1/0.17 part | D1/0.0075 part | E1 |
| Example 2 | A1/10 parts | B2/0.18 part | D1/0.0075 part | E1 |
| Example 3 | A1/10 parts | B3/0.18 part | D1/0.0075 part | E1 |
| Comparative example 1 | A1/10 parts | C1/0.2 part | D1/0.0075 part | E1 |
| Comparative example 2 | A1/10 parts | C2/0.17 part | D1/0.0075 part | E1 |
| Comparative example 3 | A1/10 parts | C3/0.21 part | D1/0.0075 part | E1 |

TABLE 2

| Example No. | Effective Sensitivity (mJ/cm$^2$) | Resolution (μm) | Cross-sectional view of resist |
|---|---|---|---|
| Example 1 | 21 | 0.16 | ◯ |
| Example 2 | 25 | 0.15 | ◯ |
| Example 3 | 25 | 0.16 | ◯ |
| Comparative example 1 | 17 | 0.15 | X |
| Comparative example 2 | 18 | 0.16 | X |
| Comparative example 3 | 36 | 0.15 | Δ |

As seen from Table 2, the resist compositions according to Examples each had well-balanced characteristics, exhibited high sensitivity and provided for a good cross-sectional view, as compared with the resist compositions according to Comparative Examples.

The sulfonium salt according to the present invention is energy-active and hence can be advantageously used as a component of resist. The chemical amplifying type positive resist composition according to the present invention is suitable for lithography employing ArF or KrF excimer laser for example and has sensitivity in good balance with a cross-sectional view of resist and hence has a high industrial value.

What is claimed is:

1. A chemical amplifying type positive resist composition comprising:

a resin which contains a structural unit having a group that is unstable to acid and which is insoluble or slightly soluble by itself in a aqueous alkali, but becomes soluble in the aqueous alkali by an action of acid;

a sulfonium salt represented by the following formula (I):

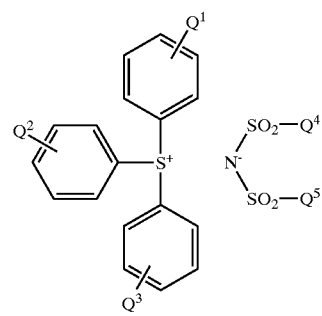

(I)

wherein $Q^1$, $Q^2$ and $Q^3$ each independently represent a hydrogen, hydroxyl, alkyl having 1 to 6 carbon atoms, or alkoxy having 1 to 6 carbon atoms, but all of $Q^1$, $Q^2$ and $Q^3$ are not the same; and $Q^4$ and $Q^5$ each independently represent a perfluoroalkyl having 1 to 8 carbon atoms; and a sulfonium salt represented by the following formula (IIc):

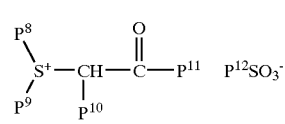

(IIc)

wherein $P^8$ and $P^9$ each independently represent an alkyl having 1 to 6 carbon atoms or a cycloalkyl having 3 to 10 carbon atoms, or when $P^8$ and $P^9$ are combined with $S^+$ to form a ring, $P^8$ and $P^9$ together with $S^+$ represent an alicyclic hydrocarbon group having 3 to 7 carbon atoms; at least one —$CH_2$— group of the alicyclic hydrocarbon group is optionally substituted with a —CO— group and at least one —$CH_2$— group of the alicyclic hydrocarbon group is optionally substituted with oxygen or sulfur; $P^{10}$ represents a hydrogen and $P^{11}$ represents an alkyl having 1 to 6 carbon atoms, a cycloalkyl having 3 to 10 carbon atoms, or an aromatic ring group optionally substituted, or when $P^{10}$ and $P^{11}$ are combined with an adjacent CHC(O) group to form a ring, $P^{10}$ and $P^{11}$ together with the CHC(O) group represent a 2-oxocycloalkyl; and $P^{12}$ represents a perfluoroalkyl having 1 to 8 carbon atoms.

2. The chemical amplifying type positive resist composition according to claim 4, further comprising an acid generator comprising at least one onium salt selected from the group consisting of a triphenylsulfonium salt and a diphenliodonium salt;

wherein said a triphenylsulfonium salt is represented by the following formula (IIa):

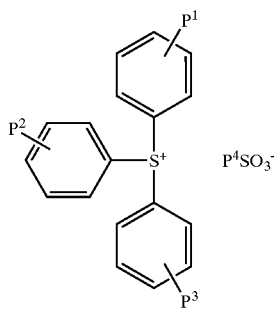

(IIa)

wherein $P^1$, $P^2$ and $P^3$ each independently represent a hydrogen, hydroxyl, alkyl having 1 to 6 carbon atoms, or alkoxy having 1 to 6 carbon atoms and $P^4SO_3^-$ represents an organic sulfonate ion; and said a diphenliodonium salt is represented by the following formula (IIb):

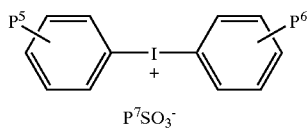

(IIb)

wherein $P^5$ and $P^6$ each independently represent a hydrogen, hydroxyl, alkyl having 1 to 6 carbon atoms, or alkoxy having 1 to 6 carbon atoms and $P^7SO_3$ represents an organic sulfonate ion.

3. The composition according to claim 1, wherein the weight ratio of the sulfonium salt represented by the formula (I) to the sulfonium salt represented by the formula (IIc) is 9:1 to 1:9.

4. The composition according to claim 1, wherein the content of the structural unit having a group that is unstable to acid in the resin is 10 to 8 mol %.

5. The composition according to claim 1, wherein the structural unit having a group that is unstable to acid in the resin is 2-alkyl-2-adamantyl (meth)acrylate or 1-(1-adamantyl)-1-alkylalkyl (meth) acrylate.

6. The composition according to claim 1, wherein the resin further comprises at least one structural unit selected from the group consisting of: a structural unit derived from p-hydroxystyrene; a structural unit derived from m-hydroxystyrene; a structural unit derived from 3-hydroxy-1-adamantyl (meth)acrylate; a structural unit derived from 3,5-dihydroxy-1-adamantyl (meth)acrylate; a structural unit derived from (meth)acryloyloxy-γ-butyrolactone wherein at least one hydrogen on the lactone ring is optionally substituted by an alkyl; and a structural unit represented by the following formulae (IIIa) and (IIIb):

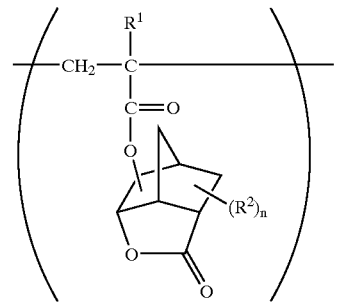

(IIIa)

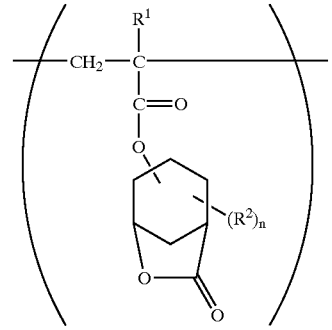

(IIIb)

wherein $R^1$ and $R^2$ each independently represent a hydrogen, methyl, or trifluoromethyl and n represents an integer from 1 to 3.

7. The composition according to claim 1, wherein the resin further comprises a structural unit derived from 2-norbornene and a structural unit derived from aliphatic unsaturated dicarboxylic anhydride.

8. The composition according to claim 1, further comprising an amine as a quencher.

9. The composition according to claim 1, further comprising a surfactant.

10. A polymerization initiator composition comprising:

a sulfonium salt represented by the following formula (I):

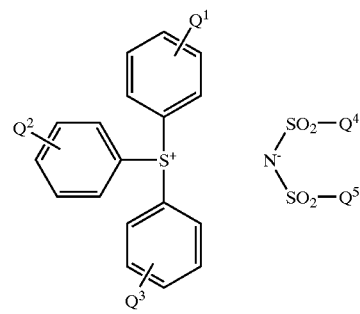

(I)

wherein $Q^1$, $Q^2$ and $Q^3$ each independently represent a hydrogen, hydroxyl, alkyl having 1 to 6 carbon atoms, or alkoxy having 1 to 6 carbon atoms, but all of $Q^1$, $Q^2$ and $Q^3$ are not the same; and $Q^4$ and $Q^5$ each independently represent a perfluoroalkyl having 1 to 8 carbon atoms;

a sulfonium salt represented by the following formula (IIc):

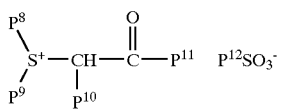 (IIc)

wherein $P^8$ and $P^9$ each independently represent an alkyl having 1 to 6 carbon atoms or cycloalkyl having 3 to 10 carbon atoms, or when $P^8$ and $P^9$ are combined with $S^+$ to form a ring, $P^8$ and $P^9$ together with $S^+$ represent an alicyclic hydrocarbon group having 3 to 7 carbon atoms; at least one —$CH^2$— group of the alicyclic hydrocarbon group is optionally substituted with a —CO— group and at least one —$CH_2$— group of the alicyclic hydrocarbon group is optionally substituted with oxygen or sulfur; $P^{10}$ represents a hydrogen and $P^{11}$ represents an alkyl having 1 to 6 carbon atoms, a cycloalkyl having 3 to 10 carbon atoms, or an aromatic ring group optionally substituted, or when $P^{10}$ and $P^{11}$ are combined with an adjacent CHC(O) group to form a ring, $P^{10}$ and $P^{11}$ together with the CHC(O) group represent a 2-oxocycloalkyl; and $P^{12}$ represents a perfluoroalkyl having 1 to 8 carbon atoms;

and a sensitizer.

* * * * *